United States Patent [19]

Hassler

[11] 4,060,763
[45] Nov. 29, 1977

[54] ARRANGEMENT FOR DETERMINING THE EFFECTIVE VALUE AND/OR THE POWER OF ELECTRICAL SIGNALS

[75] Inventor: Dieter Hassler, Erlangen, Germany

[73] Assignee: Siemens Aktiengesellschaft, Berlin & Munich, Germany

[21] Appl. No.: 614,333

[22] Filed: Sept. 17, 1975

[30] Foreign Application Priority Data

Sept. 18, 1974 Germany .............................. 2444626

[51] Int. Cl.² .......................... G01R 1/30; G01R 17/06
[52] U.S. Cl. ............................... 324/123 R; 324/99 R; 324/132
[58] Field of Search ................... 324/123 R, 132, 99 R

[56] References Cited

U.S. PATENT DOCUMENTS

3,159,787 12/1964 Sexton et al. ...................... 324/123 R
3,571,706 3/1971 Bjor ................................. 324/123 R Primary Examiner—Rudolph V. Rolinec
Assistant Examiner—Ernest F. Karlsen
Attorney, Agent, or Firm—Hill, Gross, Simpson, Van Santen, Steadman, Chiara & Simpson

[57] ABSTRACT

An arrangement for the determination of the effective value and/or the performance or power and, for example, also the cross-power of electrical signals, in particular those Doppler signals which are received in ultrasonic-Doppler blood flow measurement. The arrangement includes an amplifier for the present electrical signal regulatable in amplification which, on the one hand, is connected into a control loop or circuit for regulating the degree of amplification for the purpose of producing constant amplifier power outputs and, on the other hand, connected into a measuring circuit for determination of the degree of amplification which adjust itself at the current power constant-regulation of the amplifier.

6 Claims, 7 Drawing Figures

ARRANGEMENT FOR DETERMINING THE EFFECTIVE VALUE AND/OR THE POWER OF ELECTRICAL SIGNALS

FIELD OF THE INVENTION

The present invention relates to an arrangement for the determination of the effective value and/or the performance or power and, for example, also the cross-power of electrical signals, in particular those Doppler signals which are received in ultrasonic-Doppler blood flow measurement.

DISCUSSION OF THE PRIOR ART

Particular in ultrasonic Doppler blood flow measurement, for the determination of the medium blood flow velocity or the further magnitudes which are taken off therefrom, there must be determined the power (or also cross-power) of the Doppler signals. The Doppler NF-signals thus have a band width of about 100 Hz to 15 kHz at a dynamic range of the effective value of about 50 dB and, additionally, about 10 dB between the timed peak values and the effective value. For carrying out the squaring of that type of signal, the usual multipliers are not suitable, since for these there would be required an output dynamic range of 160 dB at a 1% error. The usual integrated multipliers, however, at a 1% error allow only about a 10 dB input voltage dynamic range.

SUMMARY OF THE INVENTION

Accordingly, it is an object of the present invention to provide an arrangement of the above-mentioned type in which, at the lowest technical requirements, there is determined from electrical signals, in particular Doppler signals, having an extremely high amplitude dynamic range, the effective value and/or the power and, upon occasion, also the cross-power, of these signals.

The foregoing object is inventively attained by means of an amplifier for the present electrical signal regulatable in amplification which, on the one hand, is connected into a control loop or circuit for regulating the degree of amplification for the purpose of producing constant amplifier power outputs and, on the other hand, connected into a measuring circuit for determination of the degree of amplification which adjust itself at the current power constantregulation of the amplifier.

In the arrangement according to the invention, due to the power constant-regulation, there is also provided a constant effective value which, as a result of the remaining low dynamic range, may be easily squared by means of the usual multipliers. The determination of this effective value is carried out in a simple manner within the measuring circuit for the degree of amplification. For this purpose, the constant output power of the variable amplifier need merely be divided by the degree of amplification of the variable amplifier which is obtained in the measuring circuit. Consquently, determination of the degree of amplification by means of a separate measuring circuit is thereby absolutely necessary since, due to the unknown regulating characteristics of the variable amplifier, the degree of amplification cannot be assumed with adequate precision from the control voltage.

The determination of the degree of amplification may be effectuated selectively in accordance with either the known time-multiplex principle, or the similarly known frequency-multiplex principle. In the time multiplex principle, for this purpose the electrical signal, as well as the signal which is won through the measuring circuits are timely staggered transmitted to the variable amplifier by means of oscillating reversing switches. Through a scanning or sensing switch at the output of the variable amplifier, which is connected synchronously with the reversing switch at the input of the variable amplifier, the signals appearing at the output of the variable amplifier are separated from each other in conformance with their staggered input into the variable amplifier. The separation is carried out in a manner whereby the electrical signal, whose effective value is to be determined, or respectively, whose power must be formed, in conducted to the control circuit for the power constant-regulation, and that the signal which emanates from the measuring circuit, after suitable amplification thereof, is again supplied into the amplification degree measuring circuit. In contradistinction with the time-multiplex principle, in the frequency-multiplex principle there is present a reversing switch in the measuring circuit which chops the measuring circuit signal into an amplitude-proportional direct current-free alternating signal of a frequency which is much higher in comparison with the highest frequency of the electrical signal, for example, 100 kHz, and then superimposes this signal on the electrical signal. Corresponding to the separation switches in the time-multiplex principle, two electrical frequency filters are thus connected to the output of the variable amplifier of which one is a low-pass filter and serves for separation of the frequency components emanating from the electrical signal, and the second is high-or band-pass filter which merely permits passage therethrough to the measuring circuit of frequency components with frequencies which are equal to or higher than the chopping frequency of the switch.

In a preferred embodiment of the invention, the control circuit contains a squaring element with a thereto connected integrating element (low-pass) for the forming of the power of the electrical signals. Should there be formed the cross-power of two signals then, in contrast therewith, the squaring element is to be replaced by a multiplier element for the two signals. Following the low-pass filter is a differential amplifier which compares the power signal of the integrating stage with a pregiven reference value and which regulates the degree of amplification of the variable amplifier with its output signal to such a value whereby the difference between the power signal in the control circuit and the reference value of the power becomes zero. The measuring circuit for the degree of amplification, in a preferred embodiment, contains in comparison therewith, in addition to the separating switch in the time-multiplex principle, or respectively, the high-pass filter in the frequency-multiplex principle, a low-pass filter for demodulation of the amplified measuring circuit signal, as well as a further differential amplifier which similarly compares the demodulated measuring circuit signal with a reference value. For a relatively low amplification of the variable amplifier, there is thus obtained a relatively large differential signal between the demodulated measuring circuit voltage and reference value. In contrast therewith, at a relatively high amplification of the variable amplifier, this differential voltage is relatively low. It is ascertainable that at the output of the operation amplifier, under the assumption of infinitely high circuit amplification, there is thus obtained a signal whose amplitude is inversely proportional to the degree of amplification of the variable amplifier which has presently been set by means of the control circuit. The signal which appears at the output of the operational amplifier in the measuring circuit is thus in a direct linear relationship with the present signal effective value. Through a squaring of the effective value there is then obtained the desired power output or performance. Since effective value and not power are indicated, the dynamic range of this signal in dB-measurement is to be reduced by a factor of two with respect to a power indication.

In a further preferred embodiment of the invention, the power of the supplied electrical signals may also be directly determined that in the current supply means of the measuring circuit signal in the variable amplifier pass through the measuring signal in the measuring circuit not only once, but a total of two times. This two-times through-passage corresponds to a squaring of the effective value. For this purpose, the previously described elements of the measuring circuits may be doubly provided in a parallel circuit connection. In lieu of the two-time passing through of the auxiliary circuit signal, for the squaring of the measuring signal there may also be provided a series connection of two separate variable amplifiers.

BRIEF DESCRIPTION OF THE DRAWINGS

Further advantages and details of the invention may now be ascertained from the following description of exemplary embodiments thereof, taken in conjunction with the accompanying drawings; in which.

DETAILED DESCRIPTION

Figure 1:
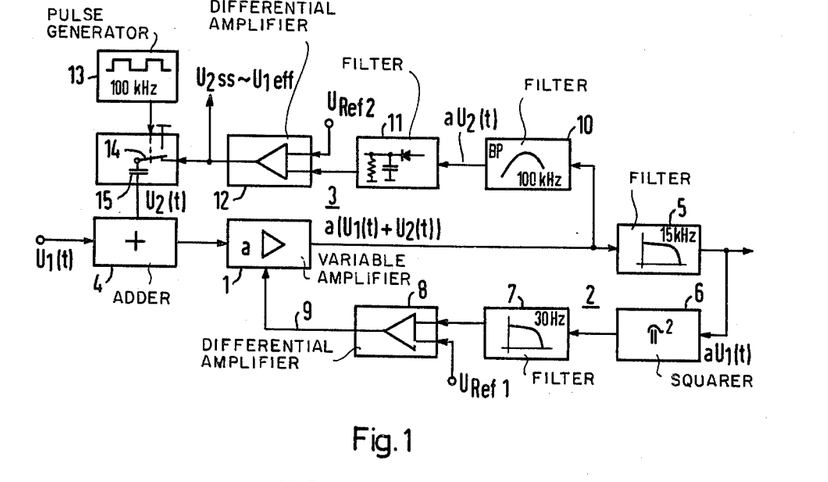
FIG. 1 illustrates a schematic circuit block diagram of an arrangement employed for determining the effective value and/or the power of a signal voltage pursuant to the frequency-multiplex principle.

Illustrated in FIG. 1 is a variable amplifier 1 which is connected into a control circuit 2 for power constant-regulation and into a measuring circuit 3 for the measurement of the amplification degree a of the variable amplifier which is currently obtained at the power constant-regulation. Across the variable amplifier 1 there runs an electrical signal $U_1(t)$, for example, a Doppler signal, whose effective value, respectively, power is to be determined, as well as a square-wave voltage $U_2(t)$ which is supplied by the measuring circuit, and whose frequency is significantly higher than the highest frequency present in the electrical signal $U_1(t)$, for example, lying at 100 kHz. The voltage $U_2(t)$ which originates from the measuring circuit is hereby superimposed on the electrical signal $U_1(t)$ in a summing element 4 which is connected ahead of the variable amplifier 1.

The control circuit 2 encompasses a 15 kHz low-pass filter 5, a squaring element 6, a 30 Hz low-pass filter 7, as well as a differential amplifier 8 having a reference voltage $U_{Ref1}$ which is equivalent to a pregiven power reference value. The 15 kHz low-pass filter serves hereby for the separation of the frequency components of the signal $U_1(t)$ from the higher frequencied components of the 100 kHz oscillation $U_2(t)$. The squaring element 6 forms the square of the output voltage of the 15 kHz low-pass filter. After integrating in the 30 Hz low pass filter 7, at the signal input of the differential amplifier 8 there thus is present a signal which represents the power of the electrical signal $U_1(t)$ appearing at the output of the 15 kHz low pass filter. The power differential signal which is delivered by the differential amplifier 8 then passes directly through the control conduit 9 to the amplification control input of the variable amplifier 1 and sets the degree of amplification thereof whereby the measured power of the signal $U_1(t)$ is equal to the set reference value $U_{Ref1}$. At the output of the 15 kHz low-pass thereby is thus provided an amplified signal $U_1(t)$ with constant power. There is obtained the relationship $$a^2 \lim_{T \to \infty} \frac{1}{T} \int_{-T}^{T} \frac{U_1{}^2(t)\, dt}{K_1} = \frac{a^2}{K_1} U_{1\,eff}^2 = U_{Ref1} \quad const.,$$

wherein $U_{1eff}$ represents the effective value of the signal $U_1(t)$, $K_1$ is a constant, and a is the degree of amplification of the variable amplifier 1 set at power constant-regulation. From the above relationship there may be easily obtained the effective value $U_{1eff}$ of the electrical signal $U_1(t)$, insofar as the degree of amplification a is known.

The determination of the degree of amplification a is effective in measuring circuit 3. The measuring circuit 3 contains a 100 kHz band pass or high-pass filter for separating the 100 kHz oscillation $U_2(t)$ from the signal $U_1(t)$. The circuit further encompasses a demodulation low-pass filter 11 with a rectifier diode, which reconverts through rectifying the oscillation a $U_2(t)$, respectively, the fundamental oscillation thereof occurring at the output of the band pass filter 10, into an amplitude-proportional direct voltage. This direct voltage is compared in a further differential amplifier 12 with a reference voltage $U_{Ref2}$. The deviation from the reference voltage is strongly amplified in the differential amplifier 12 and subsequently, by means of an analog switch which is connected in synchronism with the 100 synchronizing impulse of a pulse generator 13 (transistor, for example FET-switch), in addition to condensor 15, is again transformed into an amplitude-proportional 100 kHz square-wave oscillation which, together with the signal $U_1(t)$, again passes through the variable amplifier 1. When the amplification a of the amplifier 1 which is set by means of the regulating circuit 2 is low, then, for correlation of the measuring circuit voltage with the reference value $U_{Ref2}$, the square-wave signal $U_2(t)$ at the input of the variable amplifier must be of a high amplitude. When, in contrast therewith, the amplification a is large, then it is sufficient to presently use a low amplitude square-wave signal for effecting the correlation. The voltage $U_{2ss}$ at the output of the differential amplifier 12 in the measuring circuit 3, as a result, will always automatically adjust itself in correspondence with the reciprocal value of the amplification $a$ of the variable amplifier 1. Under the assumption of infinitely high circuit amplification, for $U_{2ss}$ there is thus obtained the relationship $$U_{2ss} = \frac{U_{Ref2}}{aK_2}$$

wherein $K_2$ again represents a constant factor. When this measure for the degree of amplification a of the variable amplifier there is introduced into the above-mentioned relationship for the power of the signal $U_1(t)$ obtained through the regulating circuit 2, there then is obtained the further relationship $$U_{2ss} = \frac{U_{Ref2}}{K_2 \sqrt{K_1 U_{Ref1}}} U_{1eff}$$

The voltage $U_{2ss}$ in the measuring circuit 2 is thus directly linearly proportional to the effective value $U_{1eff}$ of the electrical signal $U_1(t)$, and thereby provides a direct measure for this effective value. Through squaring of the signal $U_{2ss}$ (effective value signal) by means of a usual squaring element, there may be then also determined in a simple manner the power of the original signal $U_1(t)$.

The advantage of the circuit arrangement pursuant to FIG. 1 consists of in that the high total dynamic range of the signal $U_1(t)$ is divided between two circuit elements, namely, the variable amplifier 1 and a squaring element for the voltage $U_{2ss}$. Thus, only alternating current signals pass through the variable amplifier 1 which alone is of significance for the wide level distance between the noise and distortion boundary of the dynamic range. This range is by about 60 dB wider than the distance between the direct current drift and the distortion boundary. The dynamic demands on the squaring elements for the signal $U_{2ss}$ are thus low and, in a simple manner, can be realized with the usual multipliers. Since the signal $U_{2ss}$ of the measuring circuit 3 is proportional to the effective value and not directly to the power $U_1(t)$, the dynamic range of $U_{2ss}$ in the dB measure is reduced by a factor of two with respect to a power indication. The analog switch 14 must in contrast therewith operate undisturbedly through a range of about 50 dB.

The arrangement pursuant of FIG. 1 which operates in accordance with the frequency-multiplex principle, should be preferably employed for determination of the effective value, respectively, power determination of Doppler signals after effectuated side-band separation. In contrast to the time-multiplex principle, namely, in this instance the signals are correctly directly presented for further processing, for example, for a frequency evaluation pursuant to German Published Patent Specification No. 1,791,191 or pursuant to German Patent Application No. P2319724, for the purpose of determining the median value of the blood flow velocity.

Figure 2:
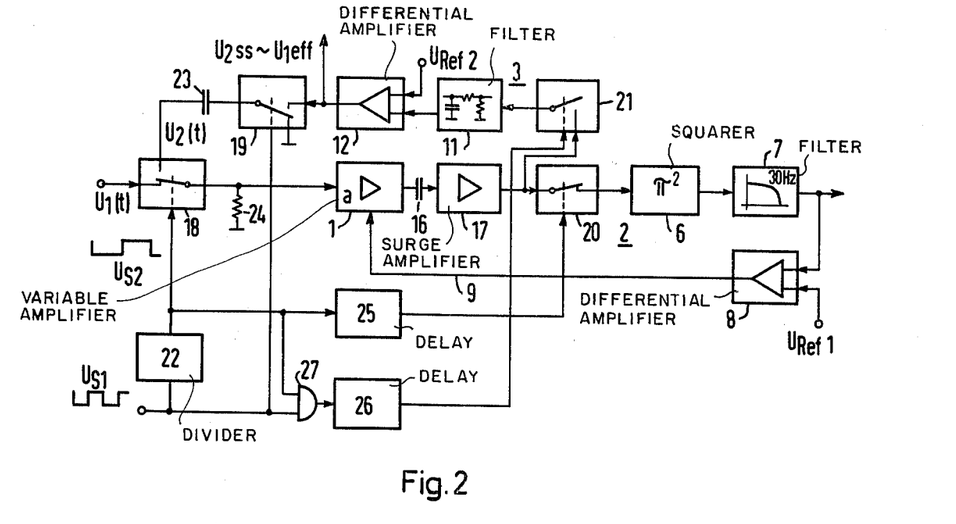
FIG. 2 shows a block diagram of an arrangement for determining the effective value and/or the power of a signal voltage pursuant to the time-multiplex principle.

Identified in FIG. 2 of the drawings by means of reference numeral 1 are again the variable amplifier, as well as the regulating circuit, respectively, measuring circuit with reference numerals 2 and 3, for the amplification $a$ of the variable amplifier. The circuit 6, 7, 8, as well as 11 and 12, correspond to those of the arrangement of FIG. 1. Further connected to the variable amplifier further, through a capacitor 16, is a surge amplifier 17.

Since, in the present instance, there is used the time-multiplex principle, connected with the variable amplifier 1 at the input side thereof are two switches 18 and 19 (for example, FET-switches) for the timely sequentially staggered infeed of the electrical signal $U_1(t)$, as well as the measuring circuit signal $U_2(t)$. For a correspondingly staggered output sided separation of the signals $U_1(t)$ and $U_2(t)$ there are provided two synchronously sensor switches 20 and 21 (for example, FET-switches).

The control of the input switches 18 and 19 is effected in best with an 8 kHz switching impulse sequence $U_{S1}$ and a 4 kHz switching impulse sequence $U_{S2}$. The 4 kHz switching impulse sequence $U_{S2}$ is hereby obtained from the switching impulse sequence $U_{S1}$ through digital frequency by section in a reducer or divider element 22.

Pursuant to FIG. 2, the switch 18 is accordingly alternatingly connected in 4 kHz impulse to the signal $U_1(t)$ and to the signal $U_2(t)$. In contrast therewith, the switch 19 oscillates in 4 kHz pulse. Through alternating charging and discharging of the capacitance 23 across an ohmic resistance 24 which is connected in parallel with the input of the variable amplifier 1, there will appear the measuring circuit signal $U_2(t)$ during one of the switching phases of the switch 18 as an 8 kHz square-wave oscillation which is bipolar at the input of the amplifier 1 whereas, during the other switching phase of the switch 18, the signal $U_1(t)$ is transmitted to the amplifier 1. The control of the sensor switch 20, respectively, 21 at the output of the variable amplifier 1 is carried out in corresponding synchronism in 4 kHz-pulse through a switching impulse reduction delay element 25, respectively in 8 kHz-pulse through a switching impulse increase delay element 26 having an AND-element 27 connected ahead thereof. The switching impulse reduction delay element 25, or respectively, the switching impulse increase delay element 26, effect a reversal of the switch 21, respectively, 20 only when possible overshots or overswings of the variable amplifier have already attenuated. Based on such overswings are erroneous measuring results, which are hereby avoided from the beginning.

In the arrangement pursuant to FIG. 2, there are carried out power constant-regulation, as well as regulating of the measuring circuit signal to amplitude values which are reciprocal to the degree of amplification of the variable amplifier, in the same manner as in the arrangement according to FIG. 1. Thereby is thus again obtained at the output of the differential amplifier 12 in the measuring circuit 3 an output signal $U_{2ss}$ which, corresponding to the signal $U_{2ss}$ of the arrangement pursuant to FIG. 1, is strongly linearly proportional to the effective value of the electrical input $U_1(t)$. Through squaring of this signal there is then again obtained the power of the signal $U_1(t)$.

When, in a modification of the arrangement pursuant to FIG. 2 (or FIG. 1), the measuring circuit signal $U_2(t)$ passes through the measuring circuit 1 not only once during a staggered phase, but a total of two times, then this two-time through pass corresponds to a square of the effective value. As the measuring circuit voltage $U_{2ss}$ there is then obtained not the effective value but the square of the effective value, the latter of which is directly proportional to the signal power.

Figure 3:
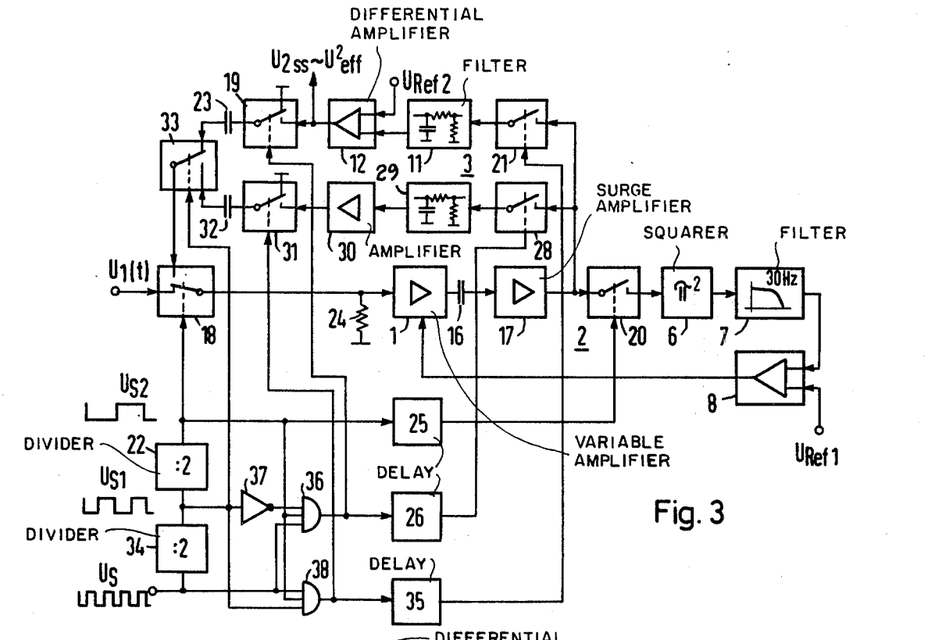
FIG. 3 illustrates a block diagram of an arrangement for determining the power of a signal voltage pursuant to the time-multiplex principle for a double passage through of the measuring circuit signal voltage.

The two-time passage of the measuring circuit signal through the amplifier 1, for example, is achieved simpliest by means of an arrangement pursuant to FIG. 3. This arrangement basically corresponds in principle to the arrangement of FIG. 2. However, in addition thereto, it contains in the measuring circuit in parallel with the previously described circuits elements 11, 12, 19, 21 and 23, a further switch 28 with an after connected demodulation low-pass filter 29, an amplifier 30 with a preconnected reversing switch 31, in addition to a capacitance 32. Furthermore, for the alternating switching over from one parallel branch to the other of the thus amplified measuring circuit 3, there is provided an additional reversing switch 33. The control arrangement for the individual switches is correspondingly enhanced by a further switching impulse generator (not shown) which produces switching impulses $U_S$ in an 16 kHz-pulse. The switching impulse sequences $U_{S1}$ and $U_{S2}$ correspond to those in the arrangement pursuant to FIG. 2.

The switching impulse sequence $U_{S2}$ is hereby again obtained from the switching impulse sequence $U_{S1}$ through digital frequency bisection in the reduction element 22. The switching impulse sequence $U_{S1}$, in contrast therewith, is hereby obtained in a corresponding manner through digital frequency bisection by means of an additional reducer element 34 from the primary switching impulse sequences $U_S$. The synchronous control of the sensor switches 20, 21 and 28 is again carried out through a switching impulse reduction delay element 25, as well as through a switching impulse increasing delay element 26, respectively 35, with correspondingly preconnected logic switching elements 36, 37, 38 (AND-elements with inverter stage).

In accordance with the illustrated circuit block diagram, through alternating crosswise closing of the switches 19 and 28, respectively the switch 21 and 31, as well as through alternating switching-over of the switch 33 in 8 kHz-pulse there is reached from one parallel branch of the measuring circuit to the other so that, in the transmission pauses of the signal $U_1(t)$ to the variable amplifier 1, the measuring circuit signal passes through the variable amplifier 1 a total of two times and whereby, during these pauses the measuring circuit signal appears amplified by the square of the amplifying factor $a$ at the differential amplifier 12. At a corresponding selection of the reference voltages $U_{Ref1}$ at the differential amplifier 8 of the regulating circuit 2, and $U_{Ref2}$ at the differential amplifier 12 of the measuring circuit 3, there is then obtained the output voltage at the differential amplifier 12.

$$U_{2ss} = \frac{U_{Ref2}}{K_1 K_2 U_{Ref1}} U^2_{1eff}.$$

The signal $U_{2ss}$ thereby is a direct measure for the square of the effective value, and thereby the power of the original signal $U_1(t)$.

In the arrangement according to FIG. 3, in lieu of one or both low-pass filters 11, respectively 29, which supply the output signal of the variable amplifier 1 in a direct voltage mode, there may be substituted an alternating voltage supplier, for example, an LC-parallel oscillating loop. With the introduction of an alternating voltage supplier, the signal information appears directly as an alternating oscillation. Thereby is eliminated at least in the lower parallel branch 28 through 32 of the measuring circuit 32 the two-time or double conversion of the alternating magnitude into a direct magnitude, and conversely. Moreover, overswings or oscillations which unavoidably occur at square-wave impulses are thus eliminated whereby simpler and, consequently, less expensive switching transistors may also be utilized as switches, and the application of digital edge or fringe delay elements for the switching impulses are obviated.

In the case of ultrasonic-Doppler blood flow measurement, the described circuitry according to FIG. 3 may preferably be utilized for power determination of the regulated Doppler signal after effectuated frequency ($\omega$-weighting for example, pursuant to German Published Patent Specification No. 1,791,191, or respectively, German Patent Application No. P 2319724). The newly created signal dynamic range which is provided by means of the evaluation filter consists of about 20 dB, so that $U_{2ss}$ fluctuates by 40 dB. This dynamic value is sufficiently small so as to be easily realized by means of the above circuit. In a modification of the described arrangement, there may also be introduced signals of smaller dynamic range in the corresponding differential amplifier for $U_{Ref1}$ and $U_{Ref2}$. In addition to the power measurement, by means of this conduit, for example, it is possible to also effect a connecting multiplication or division.

The two-time passage through the measuring circuit signal by means of a single variable amplifier for the purpose of effecting a squaring may be eliminated, when two separate variable amplifiers are provided for the electrical signal which, however, passed through by the measuring circuit signal in timed sequence. With regard to the measuring circuit signal, there is thus determined the product of the individual amplifications $a$ and $b$ of both amplifiers, so that a signal $U_{ss}$ is obtained in the measuring circuit which again is proportional to the signal power.

Figure 4:
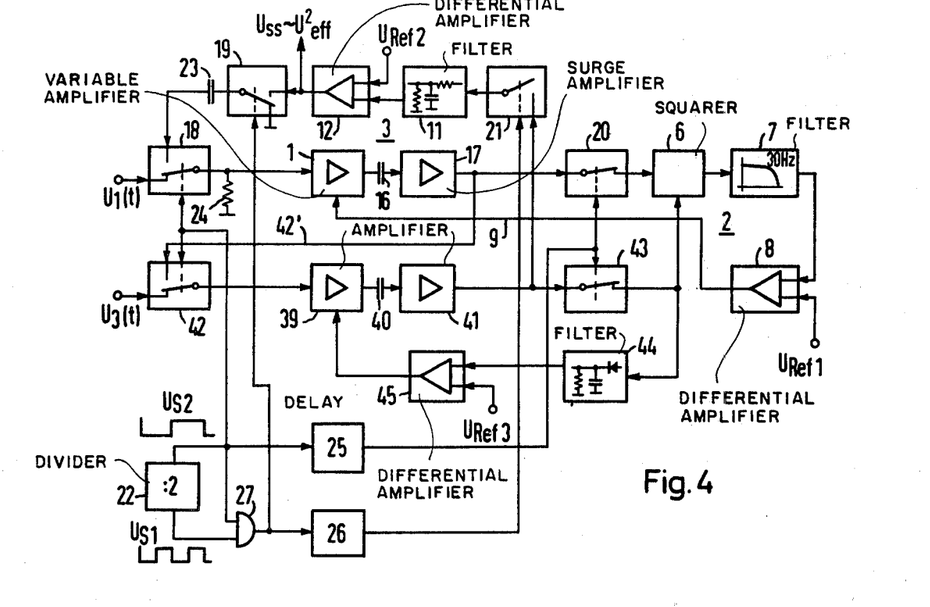
FIG. 4 is a block diagram of an arrangement for determining the cross-power of two signal voltages pursuant to the time-multiplex principle.

FIG. 4 illustrates a circuit arrangement operating according to this principle. In lieu of only the signal $U_1(t)$, there is, however, supplied to the additional amplifier 39 a second signal $U_3(t)$. The arrangement according to FIG. 4 thereby forms, in a modification, not merely the power of the signal $U_1(t)$ but the cross-power of the signals $U_1(t)$ and $U_3(t)$. The operative mode of this circuit corresponds otherwise, however, with that of the above described. In accordance therewith, the signal $U_1(t)$ is conducted to the variable amplifier 1 through a switch 18. The signal $U_3(t)$, in contrast therewith, is transmitted through a corresponding switch 42 to the amplifier 39. The switch 42 is alternatingly connected back and forth between the input terminal for the voltage $U_3(t)$ and the signal output of the variable amplifier 1. Since the switching over is carried out synchronously with the switch 18 carried out, during the feedback coupling phases of the measuring circuit signal in the amplifier 1, the switch 42 is connected to the connecting conduit 42' between the output of the amplifier 1 and the input of the amplifier 39. The measuring circuit signal thereby passes in a timed sequence through the variable amplifier 1 and, subsequently, the variable amplifier 39. Thereby is obtained the product of the amplifications $a$ and $b$ of both amplifiers. By means of the equations $$U_{Ref1} = ab \frac{U^2_{eff}}{K_1} \text{ and } U_{Ref2} = K_2 ab U_{ss}$$

there is then obtained at the output of the differential amplifier 12 the voltage $U_{ss}$ pursuant to $$U_{ss} = \frac{U_{Ref2}}{K_1 K_2 U_{Ref1}} U^2_{eff}.$$

This voltage $U_{ss}$ thereby is directly proportional to the cross-power of the two signals $U_1(t)$ and $U_3(t)$.

Under consideration of the unequality of the control characteristics of both amplifiers 1 and 31, in the arrangement according to FIG. 4, merely the variable amplifier 1 is provided for a constant-power regulation. In contrast, the variable amplifier 39 is thereby regulated to the constant conpensating value $U_{Ref3}$ through the switch 43, the low-pass filter 44 with the rectifier diode, and a differential amplifier 45 with the reference voltage $U_{Ref3}$. In the arrangement according to FIG. 4 there is recommended use of the time-multiplex procedure since in the frequency-multiplex process considerable demands are placed on the separating filters. However, a corresponding utilization of the frequency-multiplex process is, possible in principle.

Whereas, in the arrangement pursuant to FIG. 3, the circuit element 6 is a mathematical squaring element for the squaring of the electrical voltage $U_1(t)$, element 6 in the arrangement according to FIG. 4 relates to a pure multiplier element for multiplication of the voltage $U_1(t)$ with the voltage $U_3(t)$. When in a modification of the arrangement pursuant to FIG. 4 this multiplier element 6 is, in accordance with the arrangement according to FIG. 3, similarly constructed as a squaring element, then the amplification a of the amplifier 1 is regulated as previously described. When, in lieu of the signal $U_3(t)$, the amplifier 39 has also conducted thereto the signal $U_1(t)$ and if there is then formed the difference between the rectified values of the output voltage of the amplifier 1 and the amplifier 39, wherein the voltages are presently tapped off behind the switches 20 and 43, and when by means of this differential voltage there is then regulated the amplification of the amplifier 39 to the amplification of the amplifier 1, for the measuring circuit signal of the measuring circuit 3 after passing through the amplifier 1 and subsequently the amplifier 39, there is obtained the square of the amplification a of the amplifier 1. Appearing as the voltage $U_{ss}$ at the output of the differential amplifier 12 is then the square of the effective value of merely the voltage $U_1(t)$.

In the ultrasonic-Doppler blood flow measurement there must also be frequently measured the speed difference between two flows. In such a case, there are to be formed two noise or static signal $U_1(t)$ and $U_4(t)$ equal in effective value but phase displaced, in particular phase-displaced by 180° with respect to each other, which are regulated to a constant level of the cross-power; subsequently, the effective value to be formed.

The effective value is obtained when the measuring circuit signal passes through only one of two variable amplifiers which have exactly the same amplifications. Since the Doppler-NF-signal is to be processed further, there recommends itself the frequency-multiplex technique.

Figure 5:
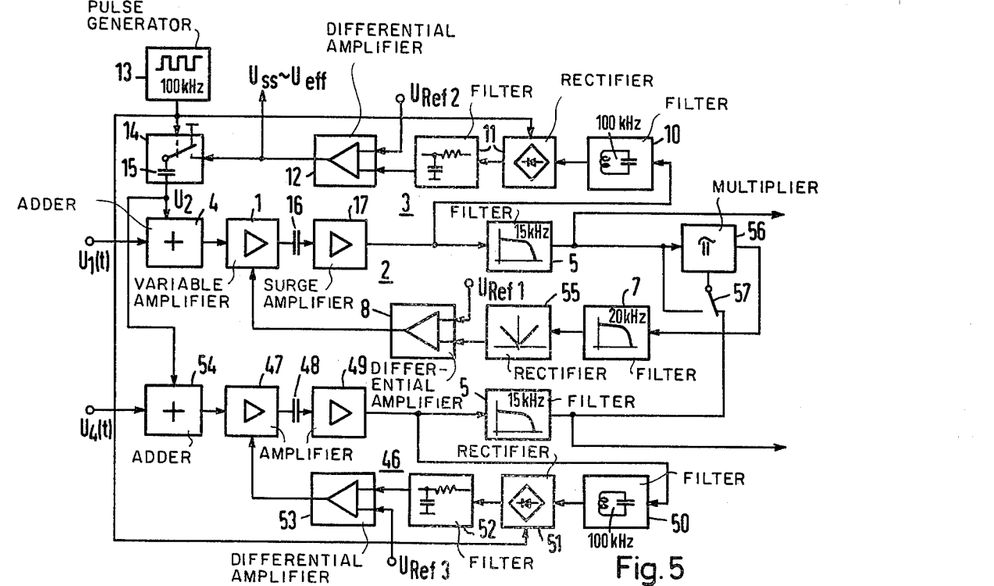
FIG. 5 is a block diagram of an arrangement in which the sum, or respectively, the difference of the side-band power of a signal voltage is regulated to a constant level, and the effective value is determined pursuant to the frequency-multiplex principle.

In the arrangement according to FIG. 5, the components 1 through 15 correspond to those of FIG. 1. In a modification of the arrangement pursuant to FIG. 1 there is, however, provided an additional control circuit 46 with a variable amplifier 47, in addition to a surge amplifier 49 which is connected thereto across a condensor 48, a further 100 kHz band-or high-pass filter 50 with after-connected rectifier 51, a demodulation low-pass filter 52, as well as a differential amplifier 53 with a reference voltage $U_{Ref3}$. The additional variable amplifier 47 has connected ahead thereof a further adding element 54 for the voltage $U_4(t)$ and for the measuring circuit square-wave oscillation $U_2(t)$ conducted thereto from a measuring circuit 3. Furthermore, additionally located in the control circuit 2 between the 30 Hz low-pass filter 7 and the differentiating amplifier 8, is a rectifier 55 for the converting of the negative voltages into a corresponding positive voltage. The surge amplifier 49, in turn, has connected thereto a 15 kHz low-pass filter 5. The output signals of both low-pass filters 5 are multiplied with each other in a multiplier element 56.

In the arrangement according to FIG. 5, the degree of amplification a of the amplifier 1 is regulated as previously described. The degree of amplification b of the amplifier 47 hereby regulates itself in a corresponding manner to the degree of amplification a of the amplifier 1, since both amplifiers have transmitted to the input sides thereof the same 100 kHz auxiliary measuring signals, and through the additional control circuit 50 through 53 both outputs of the amplifiers 1 and 47, are regulated to voltage equality. In this manner, there is obtained a regulation for 180° phase displaced signals $U_1(t)$ and $U_4(t)$ in such a manner whereby either the difference of the one side-band signal power output or their sum remains constant. The selection of constant summing power or constant differential power is effectuated by means of a reversing switch 57. When the three reference voltage $U_{Ref1}$, $U_{Ref2}$ and respectively $U_{Ref3}$ are selected to $$U_{Ref1} = a \cdot b \, U^2_{eff} K_1$$

$$U_{Ref2} = a \, K_2 U_{ss},$$

$$U_{Ref3} = b \, K_3 U_{ss}$$

then there is obtained the voltage $U_{ss}$ at the output of the differential amplifier 12 in the measuring circuit 3 as $$U_{ss} = \sqrt{\frac{U_{Ref2} U_{Ref3}}{U_{Ref1} K_1 K_2 K_3}} \cdot U_{eff}$$

There is thus obtained a signal $U_{ss}$ which is proportional to the effective value of the sum or the difference of the powers or intensities of the signals $U_1(t)$ and $U_4(t)$.

In the ultrasonic-Doppler blood flow measurement there is obtained the medium blood flow velocity, as is known, from the quotients of the power of the frequency $\omega$-weighted and not the frequency of the $\omega$-weighted Doppler signal. The determination of the power after the $\omega$-weighting may hereby be carried through a simple squaring of the $\omega$-weighted Doppler signal by means of one of the previously described arrangements. Furthermore, there is also afforded the capability that already in power constant-regulated signals (squared signal) for the numerator of the quotients may be differentiated for $\omega$-evaluation, and subsequently the cross-power formed by the unweighted and weighted squaring signals.

Figure 6:
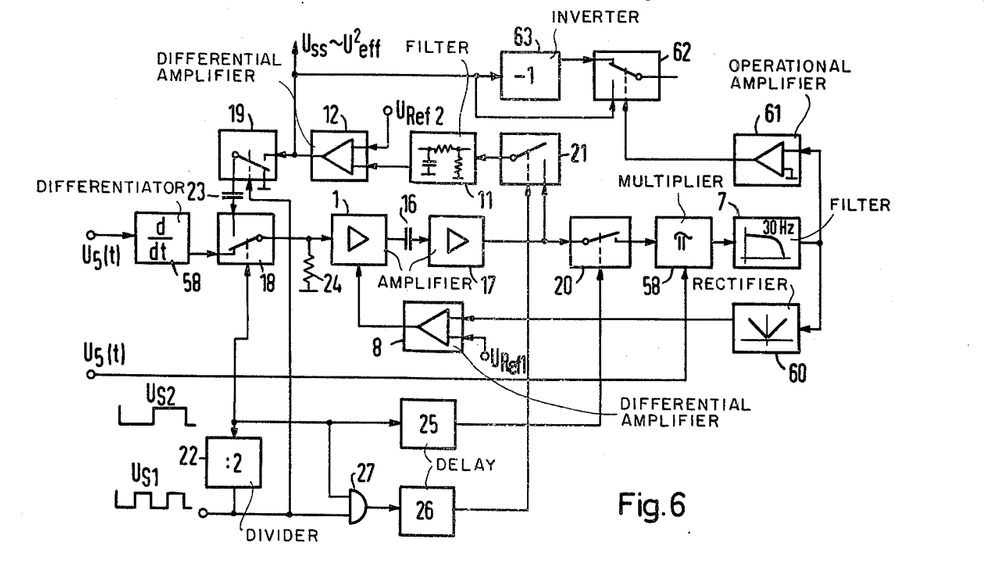
FIG. 6 is a block diagram of an arrangement for determining the difference of the $\omega$-weighted side-band power for Doppler signals pursuant to the time-multiplex principle.

In the arrangement according to FIG. 6, for this purpose there is, for example, transmitted the constant regulated squared signal $U_5(t)$, after differentiation in the differentiating element 58, through the variable amplifier 1 to a multiplier 59 and there multiplied with the directly introduced square signal $U_5(t)$. The differentiation brings an approximately 40 dB level dynamic range into the associated signal conduit. The variable amplifier 1 is now so regulated that, independently of the polarity, there a constant cross-power sets itself with the value $U_{Ref1}/K_1$. At a single pass of the measuring auxiliary signal through the measuring circuit, there is thus obtained already at the output of the differential amplifier 12 a signal $U_{ss}$ which is directly proportional to the cross-power of the weighted and unweighted signal $U_5(t)$. In the multiplication, there may be obtained positive as well as negative product signals. Since the reference voltages $U_{Ref1}$ and $U_{Ref2}$ are selected presently constantly positive, at a negative product signal the polarity of the signal must be correspondingly reversed. This is carried in the control circuit with the aid of a polarity reversing rectifier 6, and in the measuring circuit with the aid of an operational amplifier 61 recognizing the negative polarity, which connects an inverter element 63 for the voltage $U_{ss}$ through a switch 62 at a negative polarity.

Figure 7:
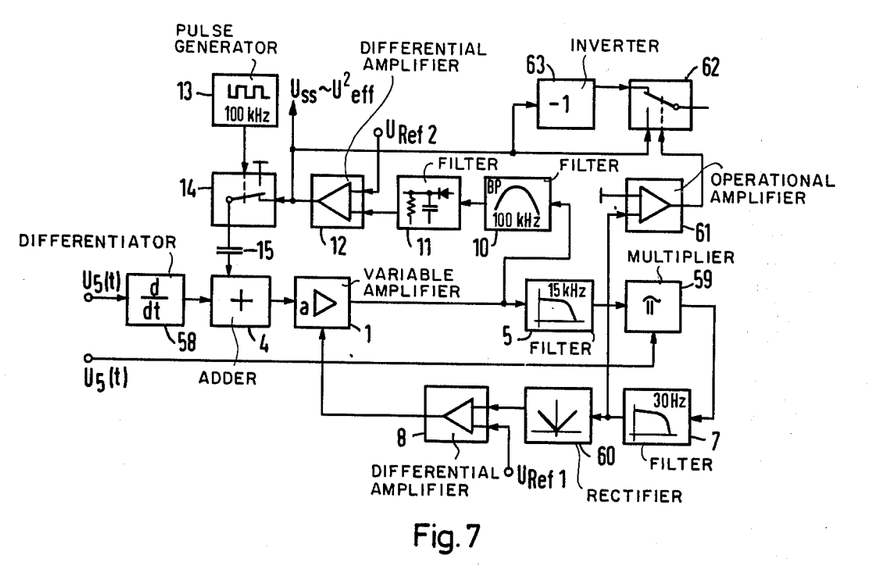
FIG. 7 is a block diagram of an arrangement for determining the difference of the $\omega$-weighted side-band power for Doppler signals pursuant to the frequency-multiplex principle.

Inasmuch as, in particular, only the measure of the power or intensity is of interest, the time-multiplex procedure finds preferred application. The operations described for the arrangement of FIG. 6 may, however, principally be also carried out pursuant to the frequency-multiplex principle. A frequency-multiplex circuit which is equivalent to that of FIG. 6 is shown in FIG. 7 of the drawings.

While there has been shown what is considered to be the preferred embodiment of the invention, it will be obvious that modifications may be made which come within the scope of the disclosure of the specification.

What is claimed is:

1. In an arrangement for determining at least one of the effective value, power intensity or cross power of one or more input electrical signals, such as Doppler signals received in ultrasonic-Doppler blood flow measurement, comprising at least one variable amplifier having a controllable amplification control circuit for regulating the degree of amplification of said variable amplifier, so as to produce a constant amplifier output power, said variable amplifier being connected to said control circuit, the arrangement further comprising a measuring circuit connected to said variable amplifier for determining the adjusted degree of amplification of the variable amplifier at said constant amplifier output power, said measuring circuit comprising: means for producing an auxiliary measuring signal; means for supplying said auxiliary measuring signal together with an input electrical signal into said variable amplifier, and means connected with the output of said variable amplifier for deriving an amplified auxiliary measuring signal from the amplified electrical signals at the output of said variable amplifier; and regulating means in said measuring circuit for regulating the amplitude of the auxiliary measuring signal in an inverse proportionality to the degree of amplification of said variable amplifier, the producing means of the measuring circuit comprising: a chopper switch for generating said auxiliary measuring signal, said switch chopping the output signal of said regulating means into an amplitude-proportional direct current-free square-wave oscillation, said chopper switch being oscillated at a frequency outside the frequency band of the input electrical signal, and being substantially higher than the highest frequency occurring in the input electrical signal; and adding means having the higher-frequencied square-wave oscillation and lower-frequencied input electrical signal superimposed therein; and means for transmitting said superimposed signals to said variable amplifier.

2. An arrangement as claimed in claim 1, said control circuit comprising a squaring element for squaring the input electrical signal as amplified in said variable amplifier for simple effective value and power formation; and a low pass filter for said squared signal being connected to said squaring element.

3. An arrangement as claimed in claim 2, comprising a differential amplifier being connected to said low pass filter in said control circuit for comparing the output signal of said low pass filter with a predetermined power reference value.

4. An arrangement as claimed in claim 3, said differential amplifier having the output thereof connected to the amplification regulating input of said variable amplifier for adjusting the degree of amplification dependent upon the power differential signal of the differential amplifier whereby the output power of said variable amplifier will correspond to the power reference value at the differential amplifier.

5. An arrangement as claimed in claim 1, comprising frequency dividing means for separating said signals at the output of said variable amplifier, said frequency dividing means including a low-pass filter in said control circuit for the frequencies of the electrical signal, and a high-pass or band-pass filter in said measuring circuit for the frequencies of said square-wave oscillation.

6. An arrangement as claimed in claim 5, the last-mentioned low-pass filter having a boundary frequency in the range of about 15 kHz and said high-pass or band-pass filter being set to frequencies of at least 100 kHz.

* * * * *